United States Patent [19]
Kelso et al.

[11] Patent Number: 5,186,712
[45] Date of Patent: Feb. 16, 1993

[54] INTRAVENOUS CATHETER LAUNCHING DEVICE

[75] Inventors: Jimmie J. Kelso, Olathe; Russell M. Hustead, Overland Park; Walter T. Miller, Leawood, all of Kans.

[73] Assignee: Kansas Creative Devices, Inc., Leawood, Kans.

[21] Appl. No.: 749,322

[22] Filed: Aug. 23, 1991

[51] Int. Cl.⁵ ............................................. A61M 5/00
[52] U.S. Cl. .................................. 604/165; 604/157; 604/164; 604/177
[58] Field of Search ............... 604/158, 161, 164–165, 604/168, 171, 173–174, 177, 180, 283, 157

[56] References Cited

U.S. PATENT DOCUMENTS

| | | |
|---|---|---|
| 3,048,171 | 8/1962 | Grace . |
| 3,714,945 | 2/1973 | Stauley . |
| 4,261,358 | 4/1981 | Vargas et al. . |
| 4,292,970 | 10/1981 | Hession, Jr. .................. 604/164 X |
| 4,362,156 | 12/1982 | Feller, Jr. et al. ................ 604/165 |
| 4,445,510 | 5/1984 | Rigley . |
| 4,557,728 | 12/1985 | Sealfon et al. . |
| 4,601,708 | 7/1986 | Jordan . |
| 4,641,663 | 2/1987 | Juhn . |
| 4,690,675 | 9/1987 | Katz .............................. 604/177 |
| 4,713,057 | 12/1987 | Huttner et al. ................. 604/164 |
| 4,787,891 | 11/1988 | Levin et al. . |
| 4,994,042 | 2/1991 | Vadher .......................... 604/165 |
| 5,026,351 | 6/1991 | Dizon ............................ 604/164 |
| 5,129,884 | 7/1992 | Dysarz .......................... 604/164 |

Primary Examiner—C. Fred Rosenbaum
Assistant Examiner—Corrine Maglione
Attorney, Agent, or Firm—Litman, McMahon & Brown

[57] ABSTRACT

An improved intravenous catheter launching device includes a body having a cavity; a hollow, sharpened needle connected to and extending outwardly from the body wherein the needle is in flow communication with the cavity; a flexible catheter having a tapered distal end and slidably telescoped over the needle such that the catheter is latchingly connected to the body by a triggering mechanism biased by a resilient extension of the body; and a compression spring operably biasing the catheter axially outwardly along the needle. Modified embodiments of the intravenous catheter launching device include a triggering mechanism biased by a second compression spring, a trigger molded integrally with a body, a rigid plunger spaced in a channel for physically launching a catheter and a semi-rigid plunger spaced in an arcuate channel for similarly launching a catheter from a minimally sized body.

15 Claims, 3 Drawing Sheets

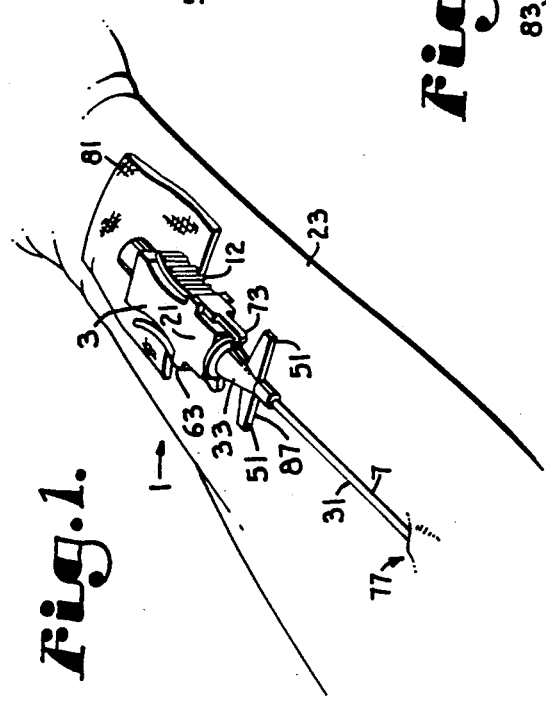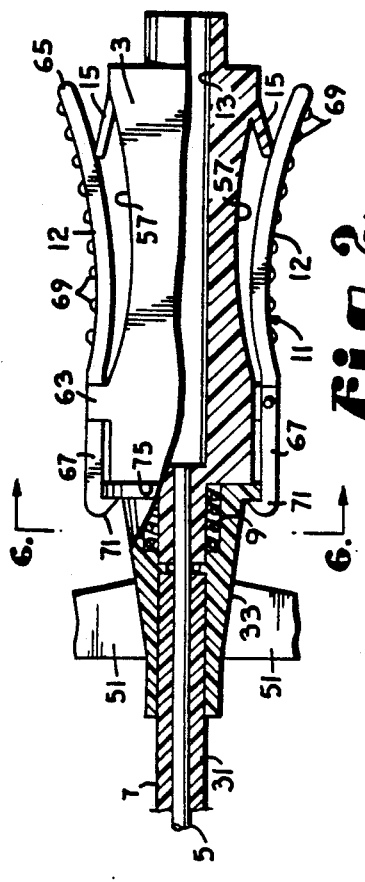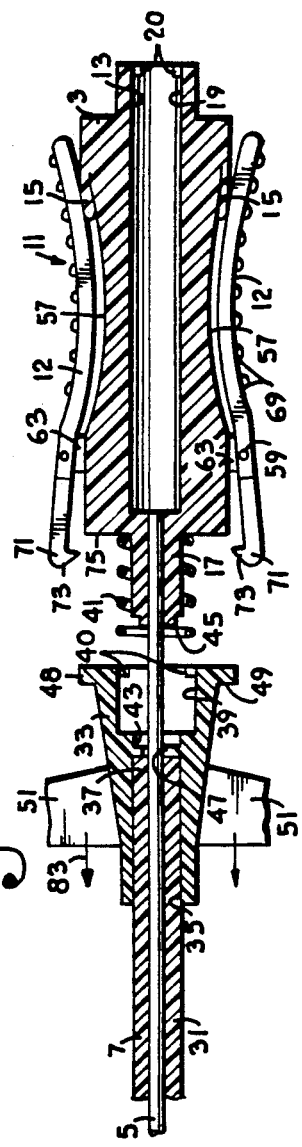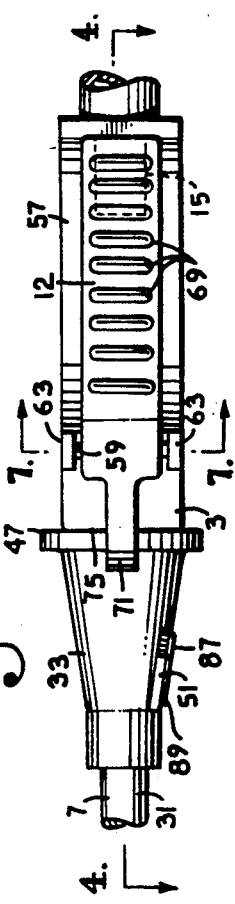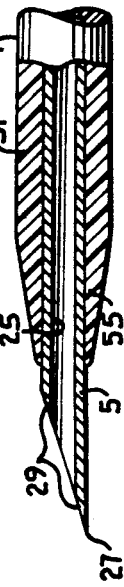

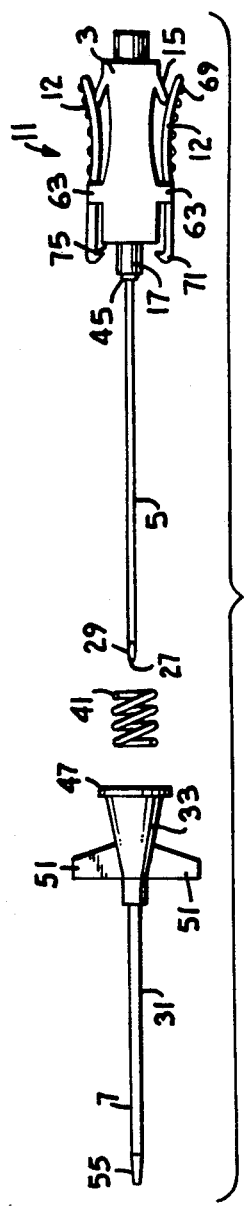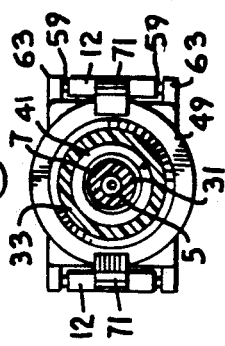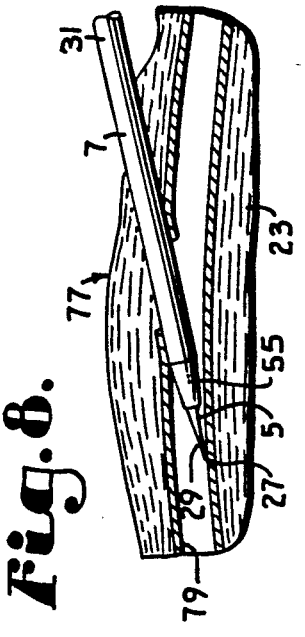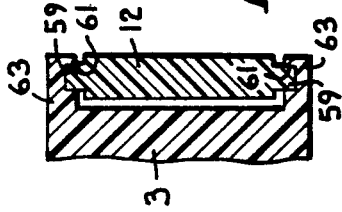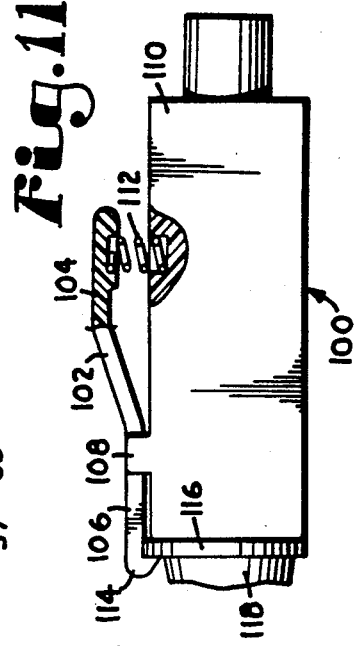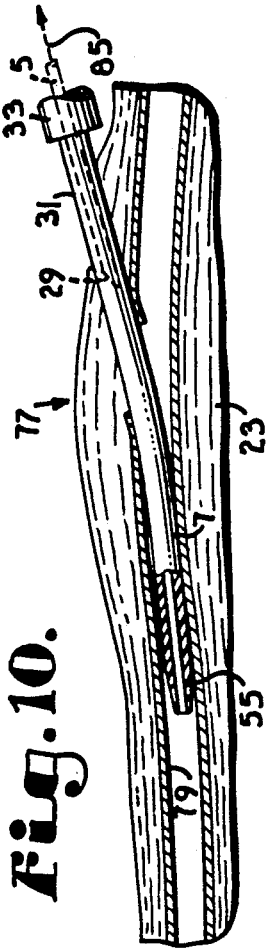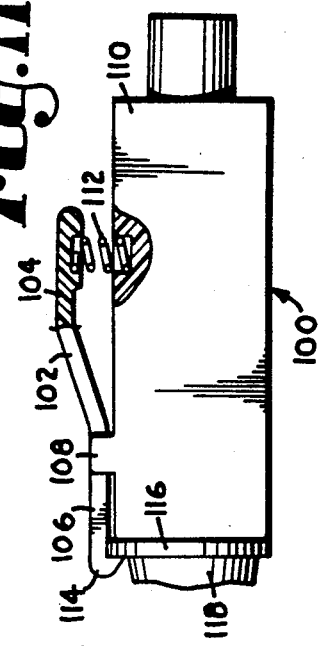

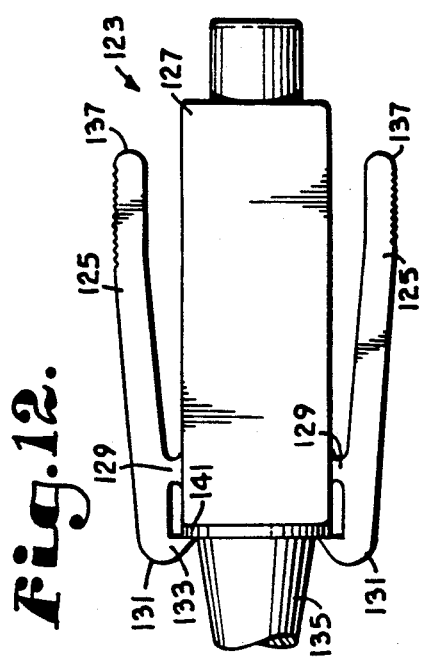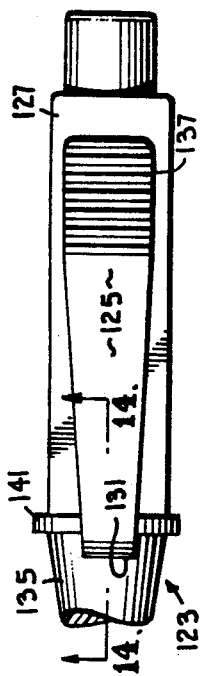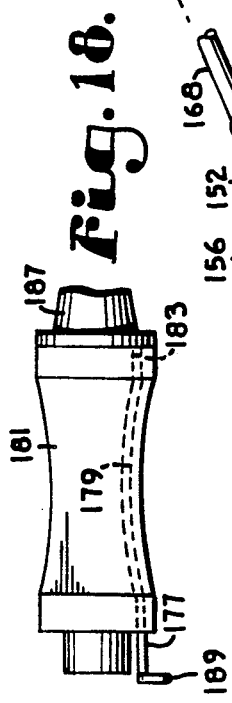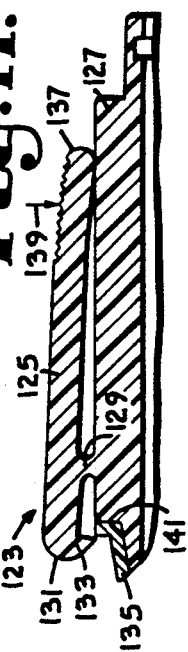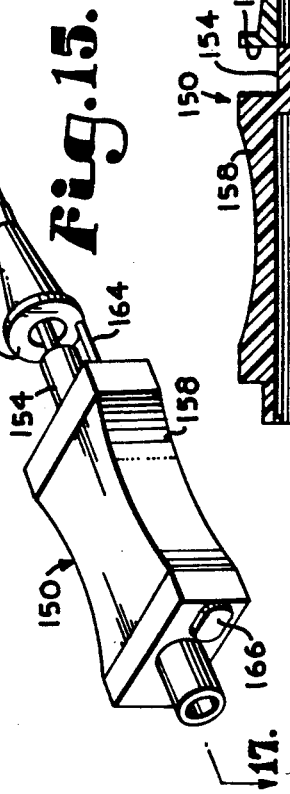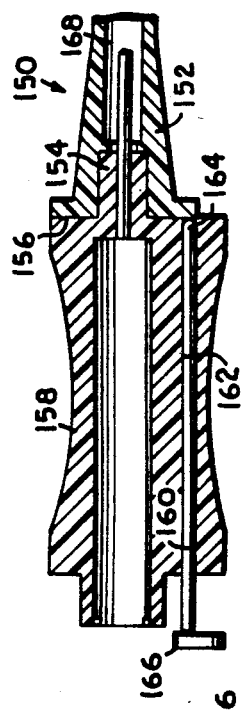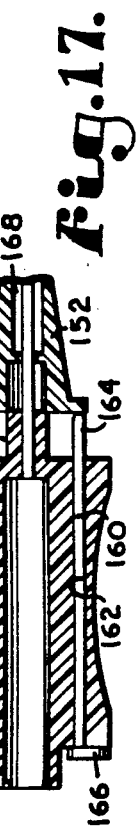

INTRAVENOUS CATHETER LAUNCHING DEVICE

FIELD OF THE INVENTION

The present invention relates to a device for establishing flow communication with a vein or artery.

BACKGROUND OF THE INVENTION

A medical procedure commonly performed on many hospital patients and also on many outpatients is the establishment of flow communication with a vein or an artery of the patient to facilitate infusion or withdrawal of various fluids therein or therefrom. For such purposes, it is not uncommon to use an intravenous catheterized catheter, which normally includes a removable needle, having the necessary rigidity to penetrate into a vein, in combination with a catheter, having the necessary flexibility needed to minimize subsequent trauma to the vein or artery.

While inserting such a device to facilitate such venipuncture and infusion, various tasks normally competitively vie for the practitioner's hands, sometimes causing the procedure to be somewhat awkward while trying to simultaneously perform the several different tasks with only two hands. Also, if the patient who is to receive the infusion is self-installing the infusion device, only one hand may be available at any one time.

Although some of the devices taught by the prior art claim to be operable with only one hand, a complicating factor is usually the separation of the catheter from the needle, with the prior art devices usually leaving much to be desired in that regard.

What is needed is a device and a method, such as a constantly applied bias between a catheter, more specifically an intravenous catheter, and a needle whereby a simple release activity mechanically and automatically initiates such separation, thus enabling a user to easily and single-handedly initiate the installation of the catheter for infusion and other purposes.

SUMMARY OF THE INVENTION

An improved intravenous catheter launching device is provided for establishing flow communication with a blood vessel for infusion purposes and the like. The intravenous catheter launching device is also useful for certain intraarterial applications.

The device includes a clear plastic body having a cavity and a sharpened, hollow needle secured such that the needle is in flow communication with the cavity. A flexible intravenous catheter, having a tapered distal end and a hub having a proximal end with a luer socket, is telescoped over the needle such that the hub is latched to the body. A compression spring confined between the catheter hub and the body operably provides an axially directed bias of the catheter relative to the needle.

A triggering mechanism comprising at least one pivotally connected trigger alongside the body provides the ability to simply and selectively release the axially directed bias, thereby mechanically, automatically, and single-handedly launching the catheter and initiating the separation of the catheter hub from the body with minimal movement of the needle point, thereby facilitating intravenous catheter insertion and minimizing trauma to the patient. The trigger is normally biased in a latching configuration by a resilient extension of the body spaced between the trigger and the body.

A first modified embodiment of the present invention includes a helical spring spaced between a trigger and a body of a catheter launching device to normally bias the trigger in a latching configuration.

A second modified embodiment of the present invention includes at least one trigger integrally molded with a body of a catheter launching device constructed of resilient material. The trigger is structured such that an integral bridge between the trigger and the body normally biases the trigger in a latching configuration.

A third modified embodiment of the present invention includes a plunger for mechanically ejecting a hub and catheter from a nub of a body of a catheter launching device.

A fourth modified embodiment of the present invention includes a semi-rigid plunger for mechanically ejecting a hub and catheter from a nub of a body of a catheter launching device such that the plunger can be routed through the body in a manner which allows reducing the size of the body.

PRINCIPAL OBJECTS AND ADVANTAGES OF THE INVENTION

Therefore, the principal objects and advantages of the present invention include: to provide a device and a method for making flow communication with a blood vessel; to provide such a device and a method for observing "flash-back"; to provide such a device and a method having a sharpened needle sheathed in a catheter; to provide such a device and a method for selectively and automatically displacing a catheter axially along a hollow needle; to provide such a device and a method having a catheter adapted for connection to and flow communication with infusion apparatus; and to generally provide such a device which is efficient and reliable, economical to manufacture, safe to use, and which generally performs the requirements of its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of an intravenous catheter launching device, according to the present invention.

FIG. 2 is an enlarged and fragmentary, top view of the intravenous catheter launching device, with portions cut away to reveal details thereof.

FIG. 3 is an enlarged and fragmentary, side elevational view of the intravenous catheter launching device.

FIG. 4 is an enlarged and fragmentary, cross-sectional view of the intravenous catheter launching device, taken generally along line 4—4 of FIG. 3.

FIG. 5 is an exploded top view of the intravenous catheter launching device.

FIG. 6 is an enlarged, cross-sectional view of the intravenous catheter launching device, taken generally along line 6—6 of FIG. 2.

FIG. 7 is a further enlarged and fragmentary, cross-sectional view of the intravenous catheter launching device, taken generally along line 7—7 of FIG. 3.

FIG. 8 is an enlarged and fragmentary, side elevational view of a needle and a catheter of the intravenous catheter launching device, having distal ends thereof inserted in a vein of a patient.

FIG. 9 is a further enlarged and fragmentary side elevational view of the needle and the catheter of the intravenous catheter launching device, with portions cut away to reveal details thereof.

FIG. 10 is an enlarged and fragmentary, side elevational view Of the catheter of the intravenous catheter launching device, with portions out away to reveal details thereof, showing the needle partially withdrawn in phantom.

FIG. 11 is a fragmentary, top view of a first modified embodiment of an intravenous catheter launching device, with portions cut away to reveal details thereof, according to the present invention.

FIG. 12 is a fragmentary, top view of a second modified embodiment of an intravenous catheter launching device, according to the present invention.

FIG. 13 is a fragmentary, side elevational view of the second modified embodiment of the intravenous catheter launching device.

FIG. 14 is a fragmentary, cross-sectional view of the second modified embodiment of the intravenous catheter launching device, taken generally along line 14—14 of FIG. 13.

FIG. 15 is a fragmentary, perspective view of a third modified embodiment of an intravenous catheter launching device, according to the present invention.

FIG. 16 is an enlarged and fragmentary, cross-sectional view of the third modified embodiment Of the intravenous catheter launching device.

FIG. 17 is a fragmentary, cross-sectional view of the third modified embodiment of the intravenous catheter launching device, showing a hub ejected from a nub thereof, taken generally along line 17—17 of FIG. 15.

FIG. 18 is a fragmentary, top view of a fourth modified embodiment of an intravenous catheter launching device, according to the present invention.

DETAILED DESCRIPTION OF THE INVENTION

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting; but merely as a basis for the claims and as a representative basis for teaching one skilled in the art to variously employ the present invention in Virtually any appropriately detailed structure.

II. Preferred Embodiment 1

The reference numeral 1 generally refers to an intravenous catheter launching device according to the present invention, as shown in FIGS. 1 to 10. The device 1 includes a body 3, injection means such as a needle 5 and a catheter 7, and launching means such as axially biasing means 9 in combination with triggering means 11, such as pair of opposing triggers 12. It is to be understood that some applications of the present invention may use only one of the triggers 12.

The body 3 is preferably constructed of transparent material having residual resiliency characteristics, such as polypropylene, polyamides, polyesters, or any other suitable material, including thermoplastics. The body 3 has a cavity 13, springs or extensions 15 extending generally outwardly therefrom, as shown in FIG. 2, and a generally cylindrically shaped nub 17 generally coaxial with, and extending outwardly from the cavity 13, as shown in FIG. 4. The cavity 13 has an end 19 which may be open to the ambient atmosphere or capped (not shown) to prevent blood spill. The end 19 may be configured as a female luer socket 20. The body 3 has at least one planar side, such as that designated by the numeral 21 in FIG. 1, such that a practitioner can observe the contents of the cavity 13 as the device 1 is used on a patient 23.

The needle 5 is hollow, such as the lumen designated by the numeral 25 as shown in FIG. 9, and has a sharpened distal end 27 having a face 29 which faces in a direction which is generally transverse to the longitudinal axis of the needle 5. The needle 5 is rigidly secured to the body 3 such that the face 29 faces in the same general direction as that faced by the planar side 21 and such that the lumen 25 is in flow communication with the cavity 13.

The catheter 7 has a tube 31 and a hub 33. The tube 31 has an inside diameter which is dimensioned slightly larger than the outside diameter of the needle 5 such that the tube 31 can be slidably telescoped over the needle 5. The hub 33 is generally conically shaped, as shown in FIG. 1, and has a first hub cavity 35 for receiving a proximal end 37 of the tube 31; a second hub cavity 39, also generally cylindrically shaped and configured as a female luer socket 40, such that a helical launching or compression spring 41 can be contained between the hub 33 and the nub 17, as hereinafter described; and a third hub cavity 43 for receiving a boss 45. A throughbore 47 provides axial, lengthwise access through the interior of the hub 33. The hub 33 has a radially extending, peripheral rib 48 having a shoulder 49 and a pair of substantially planar, tangentially extending wings 51. The spring 41 is generally connected to the nub 17 such that the spring 41 remains with the nub 41 when the hub 33 is disconnected from the body 3 as hereinafter described.

The catheter tube 31 is constructed of flexible material, such as polypropylene, polytetrafluoroethylene, or other suitable material. The proximal end 37 of the tube 3 is fixedly secured to the hub 33. A distal end 55 of the tube 31 is tapered outwardly, as shown in FIG. 9. The tube 31 is axially dimensioned such that as the hub 33 is substantially abutting the body 3, as shown in FIG. 2, the sharpened distal end 27 of the needle 5 extends beyond the distal end 55 of the tube 31, as shown in FIG. 9.

Each of the triggers 12 is pivotally mounted on opposite sides 57 of the body 3, such as by snappingly inserting a pair of opposing pegs 59 disposed on opposite sides of each of the triggers 12 into corresponding depressions 61 formed in respective posts 63 secured to the body 3, as shown in cross-section in FIG. 7. Alternatively, the triggers 12 and the posts 63 can be molded integrally with the body 3.

Each of the triggers 12 has a grip end 65 and a latch end 67. The grip end 65 generally has grip ridges 69 therealong, as shown in FIG. 3. The latch end 67 has a hook 71. The extensions 15 are configured such that each of them normally urges the grip end 65 of the respective trigger 12 outwardly from the body 3 causing the respective latch end 67 to be normally spaced in close proximity to the body 3 such that the hooks 71 latchingly engage the shoulder 49 of the hub 33 as the hub 33 is in close proximity to the body 3, as shown in FIG. 2. The triggers 12 and the extensions 15 are configured such that as the grip ends 65 of the triggers 12 are urged inwardly toward the body 3, the latch ends 67 of the triggers 12 are rotated outwardly from the body 3 such that the hooks 71 can be sufficiently spaced apart to allow the rib 48 to pass therebetween, as shown in FIG. 4.

In an application of the present invention, the needle 5, with the body 3 secured thereto and the spring 41 about the nub 17, is inserted through the interior of the hub 33 and the catheter 7. The hub 33 and the body 3 are urged toward each other, compressing the spring 41 therebetween, until the rib 48 bears against a tapered portion 73 of each of the hooks 71, forcing the latch ends 67 of the triggers 12 outwardly causing the extensions 15 to be flexed inwardly toward the body 3 by the grip ends 65 of the triggers 12.

As the hub 33 and the body 3 are further urged toward each other, the rib 48 passes into a space defined by the hooks 71 and a forward end 75 of the body 3 such that the outward bias of the extensions 15 causes the hooks 71 to snap inwardly, latching the hub 33 in close proximity to the body 3, as shown in FIGS. 2 and 3. The spring 41 is then compressed within a space defined by the cavity 39, the nub 17, and the body end 75, and provides a constant bias on the hub 33, which bias is directed axially outwardly along the needle 5.

A practitioner then selects a fleshy area, such as that designated by the numeral 77 in FIG. 1, having a vein 79 coursing therethrough. Generally, to simplify location and penetration of the vein 79, the flow of blood through the vein 79 is obstructed by applying lateral pressure by tourniquet compression or other suitable means to the vein 79 just downstream from the fleshy area 77. Also, a piece of sterile, absorbent material 81, such as gauze or the like, is sometimes positioned such that it will underlie the cavity open end 19 during the venipuncture procedure as hereinafter described.

After enlarging the vein 79, the distal ends 27 and 55 of the needle 5 and the tube 31 are urged through the fleshy area 77 and into the vein 79, as shown in FIG. 8. As the needle 5 is so inserted, the device 1 is oriented such that the needle face 29 and the window 21 are directed generally toward the practitioner such that the contents of the body cavity 13 are observable by the practitioner. Also, the needle 5 is generally inserted at an acute angle, generally less than approximately 30°, directed toward the downstream flow of the vein 79. During this phase, the needle 5 provides sufficient rigidity for penetration of the fleshy area 77 and the Vein 79.

If the needle 5 has been sufficiently inserted into the fleshy area 77 to have penetrated into the vein 79 but no blood appears in the cavity 13, generally referred to as "flash-back", then the distal end 27 of the needle 5 did not enter into the vein 79. Successive attempts are then conducted until blood does appear in the cavity 13, evidencing successful venipuncture of the vein 79. If used, the gauze 81 serves to absorb any blood leakage from the "flash-back" in the cavity 13.

After successful penetration of the vein 79, as shown in FIG. 8, the user 23 urges the grip ends 65 of the triggers 12 inwardly against the extensions 15 until the latch ends 67 of the triggers 12 are sufficiently rotated outwardly from the body 3 such that the spacing between the hooks 71 allows the peripheral rib 48 to pass therebetween. Then, the spring 41 launches the hub 33, and the catheter 7 attached thereto, away from the body 3, as indicated by the arrow designated by the numeral 83 in FIG. 4, thereby mechanically and automatically initiating separation of the catheter 7 from the needle 5. As the hub 33 and the catheter 7 are so launched, the distal end 55 of the tube 31 is generally driven further along the vein 79, as shown in FIG. 10.

The needle 5 is then manually extracted from the catheter 7 and the hub 33, as indicated by the arrow designated by the numeral 85 in FIG. 10, and discarded. If desired, the distal end 55 of the tube 31 may be further inserted into the vein 79 by appropriately displacing the hub 33 relative to the fleshy area 77 as the needle 5 is withdrawn from the fleshy area 77. The hub 33 is then connected to an infusion apparatus (not shown), or other external equipment as desired, such as by the luer socket 40, or other suitable means. The pressure applied to the vein 79 downstream from the fleshy area 77 is then released and the spacing of the catheter 7 relative to the fleshy area 77 is then generally maintained by securing the wings 51 to the patient 23 by a pressure sensitive adhesive 87 on an underlying side 89 of the wings 51, or other suitable means.

III. First Modified Embodiment 100

A first modified intravenous catheter launching device in accordance with the present invention is shown in FIG. and is generally designated by the reference numeral 100. Many of the characteristics of the first modified launching device 100 are substantially similar to those previously described for the launching device 1 and are not reiterated here in detail.

A trigger 102, having a grip end 104 and a latch end 106, is pivotally mounted between a pair of opposing posts 108 extending outwardly from a body 110. A compression spring 112 biases the grip end 104 outwardly from the body 110 such that the latch end 106 is rotated inwardly toward the body 110, causing a hook 114 to engage a rib 116 of a catheter hub 118, thereby normally retaining the catheter hub 118 in close proximity to the body 110. Biasing means, such as a compression spring (not shown) confined between the hub 118 and the body 110 provides a longitudinally directed (to the left as shown in FIG. 11) launching bias.

When desired, the grip end 104 is urged inwardly toward the body 110, causing the hook 114 and latch end 106 of the trigger 112 to be rotated outwardly from the body 110 until the hook 114 clears the rib 116 allowing a catheter (not shown) connected to the hub 118 to be launched.

IV. Second Modified Embodiment 123

A second modified intravenous catheter launching device in accordance with the present invention is shown in FIGS. 12 through 14 and is generally designated by the reference numeral 123. Many of the characteristics of the second modified launching device 123 are substantially similar to those described for other embodiments herein and are not reiterated here in detail.

At least one, and preferably two, triggers 125 are molded integrally with a body 127 of the launching device 123 with a bridge 129 integrally molded therebetween. The trigger 125, the body 127, and the bridge 129 are molded of resilient material such that a latch end 131 of the trigger 125 normally seeks a latching configuration as illustrated in FIG. 12 whereat a hook 133 of the trigger 125 latchingly engages a hub 135.

As a grip end 137 of the trigger 125 is urged inwardly toward the body 127, as illustrated by the arrow designated by the numeral 139 in FIG. 14, the latch end 131 of the trigger 125 is displaced outwardly from the body 127 such that a rib 141 of the hub 135 can be readily launched past the hook 133.

V. Third Modified Embodiment 150

A third modified intravenous catheter launching device in accordance with the present invention is shown in FIGS. 15 through 17 and is generally designated by the reference numeral 150. Many of the characteristics of the third modified launching device 150 are substantially similar to those described for other embodiments herein and are not reiterated here in detail.

A hub 152 is snugly, frictionally retained about a nub 154 such that a proximal end 156 of the hub 152 is spaced in close proximity to a body 158 of the device 150, as shown in FIG. 16.

A plunger 160 is spaced in a channel 162 which passes through the body 158 such that a launch end 164 of the plunger 160 is spaced in close proximity to the proximal end 156 of the hub 152 as a knob end 166 of the plunger 160 protrudes from the body 158, as shown in FIG. 16.

In order to launch a catheter 168, the knob end 166 is urged toward the body 158 such that the plunger 160 is slidably displaced along the channel 162, thereby forcing the launch end 164 of the plunger 160 against the hub 152 such that the hub 152 is launched from the nub 154, as illustrated in FIGS. 15 and 17.

VI. Fourth Modified Embodiment 175

A fourth modified intravenous catheter launching device in accordance with the present invention is shown in FIG. 18 and is generally designated by the reference numeral 175. Many of the characteristics of the fourth modified launching device 175 are substantially similar to those described for other embodiments herein and are not reiterated here in detail.

A plunger 177 is spaced in a channel 179 which passes through a body 181 such that a launch end 183 of the plunger 177 is spaced in close proximity to a proximal end 185 of a hub 187 as a knob end 189 of the plunger 177 protrudes from the body 181, as shown in FIG. 18. The channel 179 is generally arcuately formed in the body 181 and the plunger 177 is constructed of semi-rigid material such that the body 181 can be minimally sized for handling purposes and for economy of manufacturing costs.

To use the device 175 for its intended purposes, the knob end 189 is urged toward the body 181 such that the plunger 177 is slidably displaced along the channel 179 whereby the launch end 183 of the plunger 177 forces the hub 187 away from the body 181. It is to be understood that the plunger 177 may extend outwardly from the body 181 at any angle which allows relatively easy, slidable displacement of the plunger 177 relative to the channel 179.

It is to be understood that while certain forms of the present invention have been illustrated and described herein, it is not to be limited to the specific forms or arrangement of parts described and shown.

What is claimed and desired to be secured by Letters Patent is as follows:

1. A device for flow communication with a blood vessel of a patient for use with an infusion apparatus and/or obtaining blood specimens, comprising:
   (a) a body;
   (b) injection means having a needle sheathed in a catheter, each having a distal end for penetrating into a blood vessel of the patient; said needle having a proximal end connected to said body; said catheter having a proximal end releasably connected to said body;
   (c) launching means engaging the body and the catheter for selectively and biasingly displacing said catheter relative to said needle, said launching means including a helical compression spring having a proximate end engaging said body and a distal end engaging said catheter proximal end, said compression spring coaxially receiving said needle.

2. In an intravenous insertion device having a body and a sharpened needled sheathed in a catheter for establishing flow communication with a body vessel of a user, the improvement comprising:
   (a) launching means engaging the body and the catheter for selectively and biasingly displacing the catheter relative to the needle;
   (b) said launching means includes a triggering mechanism such that said launching means is activated by a finger of the user by urging said triggering mechanism laterally; and
   (c) said triggering mechanism includes a trigger pivotally connected to the body of the device; said trigger having first and second portions and trigger biasing means for biasing said first portion of said trigger outwardly from the body of the device and said second portion of said trigger inwardly toward the body of the device; and
   (d) said biasing means is a compression spring.

3. The intravenous insertion device according to claim 2 wherein said launching means includes a launching spring.

4. In an intravenous insertion device having a body and a sharpened needled sheathed in a catheter for establishing flow communication with a body vessel of a user, the improvement comprising:
   (a) launching means engaging the body and the catheter for selectively and biasingly displacing the catheter relative to the needle;
   (b) said launching means includes a triggering mechanism such that said launching means is activated by a finger of the user by urging said triggering mechanism laterally; and
   (c) said triggering mechanism includes a trigger pivotally connected to the body of the device; said trigger having first and second portions and trigger biasing means for biasing said first portion of said trigger outwardly from the body of the device and said second portion of said trigger inwardly toward the body of the device; and
   (d) said biasing means is a resilient extension of said body.

5. The intravenous insertion device according to claim 1 which further includes a triggering mechanism including a trigger having a hook end; said trigger molded integrally with the body of the device and connected to the body such that said hook end is normally spaced in close proximity to the body.

6. A device for flow communication with a blood vessel of a patient for use with an infusion apparatus and/or obtaining blood specimens, comprising:
(a) a body;
(b) injection means having a needle sheathed in a catheter, each having a distal end for penetrating into a blood vessel of the patient; said needle having a proximal end connected to said body; said catheter having a proximal end releasably connected to said body;
(c) launching means engaging the body and the catheter for selectively and biasingly displacing said catheter relative to said needle;
(d) at least one trigger; said trigger pivotally connected to said body; said trigger releasably connected to said catheter;
(e) trigger biasing means for biasing a portion of said trigger generally outwardly from said body; and
(f) said trigger biasing means is a compression spring.

7. A device for flow communication with a blood vessel of a patient for use with an infusion apparatus and/or obtaining blood specimens, comprising:
(a) a body;
(b) injection means having a needle sheathed in a catheter, each having a distal end for penetrating into a blood vessel of the patient; said needle having a proximal end connected to said body; said catheter having a proximal end releasably connected to said body;
(c) launching means engaging the body and the catheter for selectively and biasingly displacing said catheter relative to said needle;
(d) at least one trigger; said trigger pivotally connected to said body; said trigger releasably connected to said catheter;
(e) trigger biasing means for biasing a portion of said trigger generally outwardly from said body; and
(f) said trigger biasing means is a resilient extension of said body.

8. The device according to claim 7 wherein:
(a) said body has at least one substantially transparent and planar side; said body has a cavity; and
(b) said needle is hollow and is in flow communication with said cavity.

9. The device according to claim 8, wherein;
(a) said needle has a sharpened distal end such that an opening created thereby generally faces substantially transversely; said needle is rigidly connected to said body such that said opening faces the same general direction as that faced by said planar side of said body.

10. The device according to claim 7, wherein said proximal end of said catheter is adapted to be connected to the infusion apparatus.

11. The device according to claim 7, including:
(a) at least one wing connected to said catheter near the proximal end thereof; said wing extends generally tangentially from said catheter.

12. The device according to claim 11, including:
(a) a pressure sensitive adhesive on an underlying side of said wing.

13. The device according to claim 7, including:
(a) a launching spring spaced relative to said needle and said catheter such that said catheter is operably biased axially outwardly along said needle.

14. An intravenous launching device for establishing flow communication between an external apparatus and a blood vessel of a patient, comprising:

(a) a body having a first body end, a second body end, an axial body cavity, and a nub; said body cavity open to the ambient environment at said first body end; said nub connected to and extending outwardly from said second body end;
(b) an axially hollow needle connected to and extending outwardly from said nub; said needle in flow communication with said body cavity; said needle constructed of rigid material and having a sharpened distal end;
(c) a hub having a first hub end, a second hub end, an axial hub cavity, and a peripheral rib; said hub telescopable over said nub such that said first hub end can be disposed in abutting relationship with said second body end; said hub having a luer connection such that said hub cavity can be connected in flow communication with the external apparatus;
(d) an axially hollow catheter connected to and extending outwardly from said second hub end; said catheter constructed of flexible material and having a tapered distal end; said catheter slidably telescopable over said needle such that said distal end of said needle protrudes beyond said distal end of said catheter as said first hub end is disposed in abutting relationship with said second body end;
(e) a pair of opposing triggers, each having a hook end and a grip end; said triggers pivotally connected to said body such that said hook ends are biased toward said body and said grip ends are biased away from said body; said hook ends adapted to assume a first configuration whereat said hook ends engage said rib such that said first hub end is retained in abutting relationship with said second body end and to assume a second configuration whereat said hook ends disengage from said rib such that said first hub end is released from said abutting relationship with said second body end;
(f) a helical spring adapted to bias said hub outwardly from said body such that said catheter is launched relative to said needle as said hook ends assume said second configuration; and
(g) an opposing pair of wings extending tangentially outwardly from said hub; said wings having a pressure sensitive adhesive on one side thereof such that said hub can be removably secured to the patient.

15. A method for establishing flow communication with a blood vessel of a patient for use with an existing infusion apparatus, comprising the steps of:
(a) providing a device comprising:
(1) a body having a cavity and a substantially transparent, planar side;
(2) a hollow needle having a proximal end and a sharpened distal end; said proximal end connected to said body such that said sharpened end faces substantially in the same general direction of that faced by said transparent planar side of said body; said hollow needle is in flow communication with said cavity;
(3) a flexible catheter having a tapered distal end and at least one tangentially disposed wing; said catheter telescoped over and coaxially disposed about said needle such that said sharpened distal end of said needle operabley extends beyond said distal end of said catheter; and (4) launching means connected to said body for biasingly displacing said catheter axially outwardly along said needle; said launching means including release means for selectively activating said launching means; said launching means including a helical compression spring having a proximate end engaging said body and a distal end engaging said catheter and being generally coaxially with said needle and encircling same;

(b) externally applying pressure to the blood vessel to inhibit flow of blood therethrough such that a localized portion of said vessel is temporarily enlarged;

(c) inserting the distal end of said needle and said catheter into the enlarged portion of the vessel as evidenced by "flash-back" in said cavity as observed through said transparent planar side of said body;

(d) activating said launching means such that said catheter is urgingly displaced axially along said needle;

(e) completely removing said body and said needle while retaining said distal end of said catheter in the vessel;

(f) then removing the externally applied pressure from the blood vessel;

(g) securing said wing to the patient; and (h) connecting the infusion apparatus to said catheter.

* * * * *